US010639312B1

(12) United States Patent
O'Connor

(10) Patent No.: US 10,639,312 B1
(45) Date of Patent: May 5, 2020

(54) FINISHED PHARMACEUTICAL DOSAGE FORM OF A METHENAMINE SALT SUCH AS METHENAMINE MANDELATE

(71) Applicant: Edenbridge Pharmaceuticals, LLC, Parsippany, NJ (US)

(72) Inventor: Robert O'Connor, Pipersville, PA (US)

(73) Assignee: Edenbridge Pharmaceuticals, LLC, Parsippany, NJ (US)

( * ) Notice: Subject to any disclaimer, the term of this patent is extended or adjusted under 35 U.S.C. 154(b) by 0 days.

(21) Appl. No.: 16/705,414

(22) Filed: Dec. 6, 2019

(51) Int. Cl.
*A61K 31/205* (2006.01)
*A61K 31/53* (2006.01)
*C07D 487/18* (2006.01)
*C07C 51/41* (2006.01)

(52) U.S. Cl.
CPC ............ *A61K 31/53* (2013.01); *A61K 31/205* (2013.01); *C07C 51/41* (2013.01); *C07D 487/18* (2013.01)

(58) Field of Classification Search
CPC ...... C07D 487/18; C07C 51/41; A61K 31/205
USPC .................. 544/185, 186; 514/244
See application file for complete search history.

(56) References Cited

U.S. PATENT DOCUMENTS

| 2,124,321 | A | * | 7/1938 | Tisza | .................... | C07D 487/18 544/185 |
| 4,001,231 | A | * | 1/1977 | Diamond | .............. | C07C 51/412 544/186 |
| 2006/0198886 | A1 | * | 9/2006 | Jenkins | ................ | A61K 9/2081 424/468 |

FOREIGN PATENT DOCUMENTS

GB             512583        *  9/1939

* cited by examiner

*Primary Examiner* — Venkataraman Balasubramanian
(74) *Attorney, Agent, or Firm* — Daniel G. Worley, Jr.

(57) ABSTRACT

The present invention contemplates a high dose finished pharmaceutical dosage form comprising a methenamine salt, such as methenamine mandelate, as an active pharmaceutical ingredient wherein the methenamine salt API has a moisture content that is less than the upper limit specified in the USP. A preferred embodiment of the present invention has a moisture content that is half of the limit set forth in the USP for each particular methenamine salt. An even more preferred embodiment has a moisture content of less than or equal to one-tenth of a percent (0.1%), regardless of the methenamine salt. The present invention may include one or more pharmaceutically acceptable ingredients. The present invention also contemplates a moisture content of the high dose finished pharmaceutical dosage form that is less than one percent.

8 Claims, No Drawings

US 10,639,312 B1

FINISHED PHARMACEUTICAL DOSAGE FORM OF A METHENAMINE SALT SUCH AS METHENAMINE MANDELATE

BACKGROUND OF THE INVENTION

The use of active pharmaceutical ingredients ("APIs" or in the singular form "API") that have chemical reactivity in water in high dose tablet dosage forms where the API comprises the majority of the pharmaceutical formulation (defined as 75% w/w or more of API in a single tablet) is challenging for pharmaceutical formulation scientists. These high dose tablet dosage forms are challenging because (1) the compaction properties of the API are critical to the formation of a robust tablet dosage form, (2) the small quantity of excipient(s) per tablet makes it difficult to get suitable compression, and (3) the chemical reactivity of certain APIs makes common processing techniques for ordinary high dose tablet dosage forms unacceptable. A person of skill in the art understands that an excipient is an inert ingredient that is acceptable for use in a finished pharmaceutical dosage form.

For high dose tablet dosage forms, it is common to use the wet granulation processing technique to impart suitable compaction properties to the mixture of the active pharmaceutical ingredient(s) and the excipient(s). A person of skill in the art understands that wet granulation creates an intimate mixture of the pharmaceutical formulation ingredients that promote both improved flow and compaction properties thereby modifying the properties of the API to the greatest extent of any of the pharmaceutical processing techniques. Wet granulation often utilizes binder solutions to wet mass the formulation mixture creating, in many cases, API particles with binder on the surface of each secondary particle, so during compaction it is the binder material that makes direct contact with other binder material to form the finished tablet dosage form. These secondary API particles comprised not only of API, but of the formulation mixture, will demonstrate improved compaction properties. As defined above for high dose tablet dosage forms, the formulation mixture of the active pharmaceutical ingredient(s) and the excipient(s) contains a higher percentage of the active pharmaceutical ingredient(s), typically 75% w/w or more, when compared to the percentage of excipient(s); thus, wet granulation is particularly valuable to impart suitable compaction properties and form satisfactory finished tablet dosage forms. For active pharmaceutical ingredient(s) with sensitivity to water, however, typical aqueous-based wet granulation may not be an option because wet granulation will expose the API(s) to water.

Even direct compression, also known to the those in the art as dry blend processing, can present challenges when dealing with APIs that have chemical reactivity in water in high dose tablet dosage forms. Without the ability to modify the compaction properties of the API using wet granulation, the flow and compaction properties of the neat API become critical to the formation a robust tablet dosage form.

In direct compression, the residual moisture content of the final blend (or in the case of a high dose tablet dosage form, the moisture content of the API itself) must be considered and increasing this moisture content is typically used to improve the compaction properties of the final blend. For APIs that are sensitive to water, however, increasing moisture content is not suitable because it can result in degradation of the API. On the other hand, a simple reduction in moisture content of the API to reduce the chemical reactivity or degradation can also be counterproductive to the formation/compaction of the high dose tablet dosage form, which is why formulating a high dose tablet dosage form with an API that is sensitive to water can be a significant challenge to a pharmaceutical formulation scientist.

Methenamine salts (including mandelate and hippurate salt forms) are an example of APIs that have the abovementioned chemical reactivity in water. Methenamine salts act as urinary antibacterial agents that react in acidic aqueous medium to form ammonia and the antibacterial agent, formaldehyde. The therapeutic activity of methenamine salts also requires a high dosage in order to be effective. Commercially available tablets containing methenamine salts are available in 500 mg and 1,000 mg formulations. The mechanism of action of methenamine salts illustrates why the water content in a high dose tablet dosage form of a methenamine salt is critical. For the avoidance of doubt, the methenamine salts react in an aqueous media, so controlling the amount of water in the dosage form protects the methenamine salt from reacting with the residual water. Because the sensitivity to water is only a concern for the methenamine moiety, a formulation of any salt form of methenamine (including mandelate and hippurate) faces the same challenge with respect to water content. For ease of discussion, this specification focuses on methenamine mandelate, but a person of skill in the art understands that the concepts herein apply to any salt form of methenamine.

Following administration as a pharmaceutical tablet dosage form, methenamine mandelate is rapidly absorbed (as methenamine and mandelic acid) and excreted by the kidney to concentrate in the urine. The antibacterial therapeutic activity is primarily the result of hydrolysis of the methenamine moiety, which is maximized at a pH of 5.5 or less in the urine. Mandelic acid also provides antibacterial activity, and it aids in the effectiveness of the methenamine moiety because the mandelic acid acidifies a patient's urine. While the normal range for urine pH is 4.6-8.0 depending on the materials excreted by the kidney, the presence of mandelic acid will lower the pH of a patient's urine, which enhances the effectiveness of the methenamine moiety.

The symbiosis of the methenamine moiety and mandelic acid poses a challenge to the pharmaceutical scientist. Methenamine mandelate, like any other API, has an inherent moisture content as a bulk drug substance. In the micro environment surrounding each API crystal, the moisture/water present in the API is, in fact, a saturated solution of both methenamine and mandelic acid providing an ideal environment for hydrolysis or drug degradation. Controlling the water content of the API thus helps to prevent hydrolysis or drug degradation and this is valid for both the bulk drug substance and in the finished tablet dosage form.

The United States Pharmacopeia (USP) sets limits for moisture content of APIs. The USP monograph for methenamine mandelate establishes a specification of less than 1.5% moisture content using the general physical USP test, Loss on Drying <731>. The USP monograph for methenamine hippurate establishes a specification of less than 1.0% moisture content using the general physical USP test, Loss on Drying <731>. Controlling the water content to a specification lower than the limit specified in the USP results in a finished dosage product with less hydrolysis, which in turn decreases the potential for drug degradation and improves the shelf life of the finished dosage product.

BRIEF SUMMARY OF THE INVENTION

The present invention contemplates a high dose finished pharmaceutical dosage form comprising a methenamine salt, such as methenamine mandelate, as an active pharmaceutical ingredient wherein the methenamine salt API has a moisture content that is less than the upper limit specified in the USP. The present invention may include one or more pharmaceutically acceptable excipients. The present invention balances the need to keep moisture content low, for both the API and the resulting finished tablet dosage form, to prevent drug degradation and the need to have a drug product blend that can be compressed into the desired finished tablet dosage form.

A drug product formulation of a methenamine salt (e.g., methenamine mandelate) is disclosed in greater detail below. The present invention includes a drug product comprising an methenamine salt with a moisture content that is significantly lower than is allowed by the USP that still has suitable compaction properties resulting in a finished tablet dosage form that is viable for commercial manufacturing.

DETAILED DESCRIPTION OF THE INVENTION

The present invention contemplates a high dose finished pharmaceutical dosage form comprising a methenamine salt, such as methenamine mandelate, as an active pharmaceutical ingredient wherein the methenamine salt API has a moisture content that is less than the upper limit specified in the USP. A preferred embodiment of the present invention has a moisture content that is half of the limit set forth in the USP for each particular methenamine salt. An even more preferred embodiment has a moisture content of one-tenth of a percent (0.1%), regardless of the methenamine salt. Preferred embodiments of the present invention include tablet dosages that contain either 500 milligrams or 1,000 milligrams of a methenamine salt per tablet where the API comprises 75% w/w or more of the finished dosage form, but any amount of methenamine salt is included within this invention.

The present invention may include one or more pharmaceutically acceptable ingredients. The types pharmaceutically acceptable excipients would be understood by a person of skill in the art. Some types of excipients that may be used include diluents/binders/fillers, disintegrants, glidants, and lubricants. Exemplary diluents/binders/fillers include starch, microcrystalline cellulose, hydroxypropyl cellulose, povidone, lactose, and dicalcium phosphate. Exemplary disintegrants include starch, croscarmellose sodium, sodium starch glycolate, and cross-linked polyvinyl pyrrolidone. Exemplary glidants include silicas and talc. Exemplary lubricants include stearic acid, magnesium stearate, and sodium stearyl fumarate.

The reactivity of the methenamine salts in water form, as described above, the basis for the finished dosage product's therapeutic activity, but it is also the basis for concern in drug degradation over the shelf life of the finished tablet dosage form. Beyond controlling the moisture content of the API, the present invention seeks to control the moisture content of the finished dosage form because the water resulting from other ingredients or the process can also cause drug degradation. A preferred embodiment of the finished pharmaceutical dosage form also has a moisture content of less than 1.0 percent.

A person of skill in the art understands that reducing the moisture content of the API used in the finished tablet dosage form can have negative effects in terms of processing and compaction of the finished tablet dosage form. Reducing the moisture content of the API or the finished dosage product is not a practical solution if a finished tablet dosage form cannot be made, e.g., if the low moisture formulation(s) cannot be compressed into a finished tablet dosage form. One critical aspect of this invention is the balance between using a high dose API with a low moisture content specification and designing a suitable pharmaceutical tablet formulation. This balance is not presented in the prior art and would not be apparent to a person of skill in the art.

The following examples are provided to help understand the invention but are not intended to limit the scope of the invention.

Example 1

The formula and process of one exemplary embodiment of the present invention is described below.

|  | Mg/tablet | Percent (%) |
|---|---|---|
| Active Pharmaceutical Ingredient |  |  |
| Methenamine mandelate | 1000.0 | 75.00 |
| Excipients |  |  |
| Microcrystalline cellulose 50 μm | 320.0 | 24.00 |
| Magnesium stearate | 13.3 | 1.00 |
| Total | 1333.3 | 100.00 |

The first two materials (methenamine mandelate and microcrystalline cellulose 50 μm) are charged into a v-blender. The materials are mixed until sufficiently dispersed. The magnesium stearate is passed through a 40 mesh screen and pre-blend with a small portion of the blended materials in the v-blender. Add pre-blend to remaining materials in the v-blender and mix until adequately dispersed. The final blend is discharged from the blender and charged into the hopper of a tablet press to compact into finished tablet dosage forms.

320.0 milligrams of microcrystalline cellulose 50 μm was added in this example. For a tablet with 1,000 mg of API such as the tablet in Example 1, the amount of this excipient could range from 200 to 350 milligrams. 13.3 milligrams of magnesium stearate was added in this example. For a tablet with 1,000 mg of API such as the tablet in Example 1, the amount of this excipient could range from 7 to 25 milligrams.

Example 2

The formula and process of another exemplary embodiment of the present invention is described below.

|  | Mg/tablet | Percent (%) |
|---|---|---|
| Active Pharmaceutical Ingredient |  |  |
| Methenamine mandelate | 500.0 | 80.00 |
| Excipients |  |  |
| Microcrystalline cellulose 50 μm | 119.0 | 19.04 |
| Magnesium stearate | 6.0 | 0.96 |
| Total | 625.0 | 100.00 |

The first two materials (methenamine mandelate and microcrystalline cellulose 50 μm) are charged into a v-blender. The materials are mixed until sufficiently dispersed. The magnesium stearate is passed through a 40 mesh screen and pre-blend with a small portion of the blended materials in the v-blender. Add pre-blend to remaining materials in the v-blender and mix until adequately dispersed. The final blend is discharged from the blender and charged into the hopper of a tablet press to compact into finished tablet dosage forms.

119.0 milligrams of microcrystalline cellulose 50 μm was added in this example. For a tablet with 500 mg of API such as the tablet in Example 2, the amount of this excipient could range from 75 to 150 milligrams. 6.0 milligrams of magnesium stearate was added in this example. For a tablet with 500 mg of API such as the tablet in Example 2, the amount of this excipient could range from 3 to 13 milligrams.

Example 3

The formula and process of another exemplary embodiment of the present invention is described below.

|  | Mg/tablet | Percent (%) |
| --- | --- | --- |
| Active Pharmaceutical Ingredient |  |  |
| Methenamine mandelate | 1000.0 | 86.22 |
| Excipients |  |  |
| Microcrystalline cellulose 50 μm | 60.0 | 5.17 |
| Microcrystalline cellulose 20 μm | 60.0 | 5.17 |
| Hydroxypropyl cellulose | 20.0 | 1.72 |
| Magnesium stearate | 20.0 | 1.72 |
| Total | 1160.0 | 100.00 |

The first four materials (methenamine mandelate, microcrystalline cellulose 50 μm, microcrystalline cellulose 20 μm, and hydroxypropyl cellulose) are charged into a v-blender. The materials are mixed until sufficiently dispersed. The magnesium stearate is passed through a 40 mesh screen and pre-blended with a small portion of the blended materials in the v-blender. Add pre-blend to remaining materials in the v-blender and mix until adequately dispersed. The final blend is discharged from the blender and charged into the hopper of a tablet press to compact into finished tablet dosage forms.

60.0 milligrams of microcrystalline cellulose 50 μm was added in this example. For a tablet with 1,000 mg of API such as the tablet in Example 3, the amount of this excipient could range from 10 to 110 milligrams. 60.0 milligrams of microcrystalline cellulose 20 μm was added in this example. For a tablet with 1,000 mg of API such as the tablet in Example 3, the amount of this excipient could range from 10 to 110 milligrams. 20.0 milligrams of hydroxypropyl cellulose was added in this example. For a tablet with 1,000 mg of API such as the tablet in Example 3, the amount of this excipient could range from 5 to 50 milligrams. 20.0 milligrams of magnesium stearate was added in this example. For a tablet with 1,000 mg of API such as the tablet in Example 3, the amount of this excipient could range from 6 to 24 milligrams.

Example 4

The formula and process of another exemplary embodiment of the present invention is described below.

|  | Mg/tablet | Percent (%) |
| --- | --- | --- |
| Active Pharmaceutical Ingredient |  |  |
| Methenamine mandelate | 1000.0 | 83.32 |
| Excipients |  |  |
| Microcrystalline cellulose 50 μm | 60 | 5.00 |
| Microcrystalline cellulose 20 μm | 60 | 5.00 |
| Hydroxypropyl cellulose | 26 | 2.17 |
| Sodium Starch Glycolate | 26 | 2.17 |
| Colloidal Silicon Dioxide | 8 | 0.67 |
| Magnesium stearate | 20 | 1.67 |
| Total | 1200.0 | 100.00 |

The first five materials (methenamine mandelate, microcrystalline cellulose 50 μm, microcrystalline cellulose 20 μm, hydroxypropyl cellulose, and sodium starch glycolate) are charged into a v-blender. The materials are mixed until sufficiently dispersed. The colloidal silicon dioxide and magnesium stearate are passed through a 40 mesh screen and pre-blended with a small portion of the blended materials in the v-blender. Add pre-blend to remaining materials in the v-blender and mix until adequately dispersed. The final blend is discharged from the blender and charged into the hopper of a tablet press to compact into finished tablet dosage forms.

60 milligrams of microcrystalline cellulose 50 μm was added in this example. For a tablet with 1,000 mg of API such as the tablet in Example 4, the amount of this excipient could range from 10 to 110 milligrams. 60 milligrams of microcrystalline cellulose 20 μm was added in this example. For a tablet with 1,000 mg of API such as the tablet in Example 4, the amount of this excipient could range from 10 to 110 milligrams. 26 milligrams of hydroxypropyl cellulose was added in this example. For a tablet with 1,000 mg of API such as the tablet in Example 4, the amount of this excipient could range from 5 to 50 milligrams. 26 milligrams of sodium starch glycolate was added in this example. For a tablet with 1,000 mg of API such as the tablet in Example 4, the amount of this excipient could range from 6 to 44 milligrams. 8 milligrams of colloidal silicon dioxide was added in this example. For a tablet with 1,000 mg of API such as the tablet in this Example 4, the amount of colloidal silicon dioxide could range from 1 to 16 milligrams. 20 milligrams of magnesium stearate was added in this example. For a tablet with 1,000 mg of API such as the tablet in Example 4, the amount of this excipient could range from 6 to 24 milligrams.

What is claimed is:

1. A high dose finished pharmaceutical dosage form comprising methenamine mandelate as an active pharmaceutical ingredient wherein the methenamine mandelate active pharmaceutical ingredient has a moisture content of no more than one-tenth of a percent and wherein the high dose finished pharmaceutical dosage form has a total moisture content of less than one percent.

2. A high dose finished pharmaceutical dosage form of claim 1 wherein the high dose finished pharmaceutical dosage form is a tablet.

3. A high dose finished pharmaceutical dosage form comprising at least one pharmaceutically acceptable excipient and methenamine mandelate as an active pharmaceutical ingredient wherein the methenamine mandelate active pharmaceutical ingredient has a moisture content of no more than one-tenth of a percent and wherein the high dose finished pharmaceutical dosage form has a total moisture content of less than one percent.

4. A high dose finished pharmaceutical dosage form of claim 3 wherein the high dose finished pharmaceutical dosage form is a tablet.

5. A high dose finished pharmaceutical dosage form of claim 3 wherein the pharmaceutically acceptable excipient is a binder.

6. A high dose finished pharmaceutical dosage form of claim 3 wherein the pharmaceutically acceptable excipient is a lubricant.

7. A high dose finished pharmaceutical dosage form of claim 3 wherein the pharmaceutically acceptable excipient is a binder or a lubricant.

8. A high dose finished pharmaceutical dosage form of claim 3 wherein the pharmaceutically acceptable excipient is a binder or a lubricant and wherein the high dose finished pharmaceutical dosage form is a tablet.

* * * * *